United States Patent [19]
Lubowitz et al.

[11] Patent Number: 5,618,907
[45] Date of Patent: Apr. 8, 1997

[54] THALLIUM CATALYZED MULTIDIMENSIONAL ESTER OLIGOMERS

[75] Inventors: Hyman R. Lubowitz, Rolling Hills Estates, Calif.; Clyde H. Sheppard, Bellevue; Ronald R. Stephenson, Kirkland, both of Wash.

[73] Assignee: The Boeing Company, Seattle, Wash.

[21] Appl. No.: 461,335

[22] Filed: Jun. 5, 1995

Related U.S. Application Data

[60] Division of Ser. No. 176,518, Apr. 1, 1988, which is a continuation-in-part of Ser. No. 810,817, Dec. 17, 1985, abandoned, which is a continuation-in-part of Ser. No. 726,258, Apr. 23, 1985, abandoned.

[51] Int. Cl.$^6$ .............................. C08G 63/00; C08G 63/68
[52] U.S. Cl. .............................. 528/282; 528/296; 560/76; 560/82; 560/85; 560/86; 560/88
[58] Field of Search ............................ 528/275, 296, 528/282; 560/76, 82, 85, 86, 88

[56] References Cited

U.S. PATENT DOCUMENTS

| | | |
|---|---|---|
| H183 | 1/1987 | Karasz et al. . |
| Re. 29,316 | 7/1977 | Bargain et al. . |
| Re. 30,922 | 5/1982 | Heilman et al. . |
| Re. 34,820 | 1/1995 | Lubowitz et al. ............ 528/322 |
| 3,105,839 | 10/1963 | Renner . |
| 3,236,705 | 2/1966 | Gilman et al. . |
| 3,236,808 | 2/1966 | Goldberg et al. . |
| 3,262,914 | 7/1966 | Goldberg et al. . |
| 3,265,708 | 8/1966 | Stiteler . |
| 3,267,081 | 8/1966 | Rudner et al. . |
| 3,313,783 | 4/1967 | Iwakura et al. . |
| 3,354,129 | 11/1967 | Edmonds et al. . |
| 3,355,272 | 11/1967 | D'Alessandro . |
| 3,386,969 | 6/1968 | Levine . |
| 3,408,349 | 10/1968 | Matsunaga . |
| 3,431,235 | 3/1969 | Lubowitz . |
| 3,435,003 | 3/1969 | Craven . |
| 3,449,442 | 6/1969 | Williams et al. . |
| 3,450,711 | 6/1969 | Megna et al. . |

(List continued on next page.)

FOREIGN PATENT DOCUMENTS

| | | |
|---|---|---|
| 1175998 | 9/1984 | Canada . |
| 1269576 | 5/1990 | Canada . |
| 0152372 | 1/1985 | European Pat. Off. . |
| 0154506 | 9/1985 | European Pat. Off. . |
| 0175484 | 3/1986 | European Pat. Off. . |
| 0067976 | 3/1987 | European Pat. Off. . |
| 0283636 | 1/1988 | European Pat. Off. . |
| 0289695 | 1/1988 | European Pat. Off. . |
| 0277476 | 8/1988 | European Pat. Off. . |
| 0292434 | 11/1988 | European Pat. Off. . |
| 0289798 | 11/1988 | European Pat. Off. . |
| 0292677 | 11/1988 | European Pat. Off. . |
| 0266662 | 11/1988 | European Pat. Off. . |
| 0294555 | 12/1988 | European Pat. Off. . |
| 0132547 | 2/1989 | European Pat. Off. . |
| 0305882 | 3/1989 | European Pat. Off. . |
| 0311735 | 4/1989 | European Pat. Off. . |
| 0310735 | 4/1989 | European Pat. Off. . |
| 0309649 | 4/1989 | European Pat. Off. . |
| 0317754 | 5/1989 | European Pat. Off. . |
| 0323540 | 7/1989 | European Pat. Off. . |
| 0336856 | 10/1989 | European Pat. Off. . |
| 0405128 | 1/1991 | European Pat. Off. . |
| 0418406 | 3/1991 | European Pat. Off. . |
| 0334778 | 4/1992 | European Pat. Off. . |

(List continued on next page.)

OTHER PUBLICATIONS

St. Clair, et al., *Additives Lower Pickup of Moisture by Polyimides*, NASA Tech Briefs, 80–81, Apr., 1989.

Heidemann, "Oligomers" Encyclopedia of Polymer Science and Technology vol. 9 Molding to Petroleum Resins 485–506, 1968.

*Second–generation polyimide raises continuous–use temperatures,* Advanced Composites, May/Jun. 1988.

Vanucci et al., *700° F. Properties of Autoclave Cured PMR–II Composites,* NASA Tech. Memo 100923, Sep., 1988.

Vanucci, *PMR Polyimide Compositions for Improved Performance at 371° C.* NTIS N87–16071, Apr., 1987.

Elsenbaumer et al., *Highly Conductive Meta Derivatives of Poly(phenylene Sulfide),* J. Polymer Sci: Polymer Phys. Ed., vol. 20, 1781–1787, 1982.

Patel et al., *Poly–Schiff Bases, I. Preparation of Poly–Schiff Bases from 4,4'–Diacetyl Diphenyl Ether (DDE) with Various Diamines* J. of Polymer Sci: Polymer Chem. Ed., vol. 20, 1985–1992, 1982.

Walton, *A New Conjugated Network Polymer as an Electrical Conductor and Thermally Stable Plastic,* Am. Chem. Soc. Org. Coat Plast. Chem., vol. 42, 595–599, 1980.

Lubowitz et al., *Novel High Temperature Matrix Materials.*

Serafini et al., *Thermally Stable Polyimides from Solutions of Monomeric Reactants,* Journal of Applied Polymer Science, vol. 16, pp. 905–915, 1972.

(List continued on next page.)

Primary Examiner—Jeffrey C. Mullis
Attorney, Agent, or Firm—John C. Hammar

[57] ABSTRACT

The yield of fully substituted, multidimensional aromatic hubs in the condensation of hydroxyl and acid halide functionalities is improved by adding a thallium catalyst, such as thallium ethoxide (Tl—$OC_2H_5$), in the solvent.

6 Claims, No Drawings

U.S. PATENT DOCUMENTS

| | | |
|---|---|---|
| 3,453,236 | 7/1969 | Culbertson . |
| 3,454,673 | 7/1969 | Schmidt . |
| 3,458,486 | 7/1969 | Ray et al. . |
| 3,461,461 | 8/1969 | Anthony et al. . |
| 3,528,950 | 9/1970 | Lubowitz . |
| 3,530,087 | 9/1970 | Hayes et al. . |
| 3,536,670 | 10/1970 | Aeiony et al. . |
| 3,562,223 | 2/1971 | Bargain et al. . |
| 3,563,951 | 2/1971 | Dormagen et al. . |
| 3,565,549 | 2/1971 | Lubowitz et al. . |
| 3,592,841 | 7/1971 | Broadhead . |
| 3,598,768 | 8/1971 | Bach . |
| 3,609,181 | 9/1971 | Lubowitz et al. . |
| 3,616,193 | 10/1971 | Lubowitz et al. . |
| 3,624,042 | 11/1971 | Lubowitz et al. . |
| 3,631,222 | 12/1971 | Vogel . |
| 3,632,428 | 1/1972 | Lubowitz et al. . |
| 3,635,891 | 1/1972 | Lubowitz et al. . |
| 3,641,207 | 2/1972 | Lauchlan . |
| 3,647,529 | 3/1972 | Lubowitz et al. . |
| 3,652,710 | 3/1972 | Holub . |
| 3,658,764 | 4/1972 | Bargain et al. . |
| 3,658,938 | 4/1972 | Kwiatkowski et al. . |
| 3,663,507 | 5/1972 | Vogel . |
| 3,689,464 | 9/1972 | Holub et al. . |
| 3,697,308 | 10/1972 | Lubowitz et al. . |
| 3,697,345 | 10/1972 | Lubowitz et al. . |
| 3,699,074 | 10/1972 | Lubowitz et al. . |
| 3,699,075 | 10/1972 | Lubowitz . |
| 3,708,370 | 1/1973 | Lubowitz et al. . |
| 3,708,439 | 1/1973 | Sayigh et al. . |
| 3,708,459 | 1/1973 | Lubowitz . |
| 3,729,446 | 4/1973 | Holub et al. . |
| 3,745,149 | 7/1973 | Serafini et al. . |
| 3,748,311 | 7/1973 | Burns et al. . |
| 3,748,312 | 7/1973 | Burns et al. . |
| 3,749,735 | 7/1973 | Loria . |
| 3,757,088 | 9/1973 | Osborn . |
| 3,759,777 | 9/1973 | Lubowitz et al. . |
| 3,761,441 | 9/1973 | D'Alessandro et al. . |
| 3,763,101 | 10/1973 | Jones et al. . |
| 3,766,441 | 10/1973 | D'Allessander et al. . |
| 3,770,697 | 11/1973 | Holub et al. . |
| 3,772,250 | 11/1973 | Economy et al. . |
| 3,773,718 | 11/1973 | Klebe et al. . |
| 3,781,240 | 12/1973 | Lubowitz et al. . |
| 3,781,249 | 12/1973 | Lubowitz . |
| 3,803,081 | 4/1974 | Lubowitz . |
| 3,812,159 | 5/1974 | Lubowitz . |
| 3,827,927 | 8/1974 | Lubowitz et al. . |
| 3,839,287 | 10/1974 | Kwiatkowski et al. . |
| 3,843,593 | 10/1974 | Shell et al. . |
| 3,847,867 | 11/1974 | Heath et al. . |
| 3,847,869 | 11/1974 | Williams, III . |
| 3,853,815 | 12/1974 | Lubowitz . |
| 3,859,252 | 1/1975 | Cho . |
| 3,879,349 | 4/1975 | Bilow et al. . |
| 3,879,393 | 4/1975 | Havera . |
| 3,879,428 | 4/1975 | Heath et al. . |
| 3,887,582 | 6/1975 | Holub et al. . |
| 3,890,272 | 6/1975 | D'Alelio . |
| 3,895,064 | 7/1975 | Brode et al. . |
| 3,896,147 | 7/1975 | Stephen . |
| 3,897,395 | 7/1975 | D'Alelio . |
| 3,909,507 | 9/1975 | Betts et al. . |
| 3,914,334 | 10/1975 | Lubowitz et al. . |
| 3,919,177 | 11/1975 | Campbell . |
| 3,920,768 | 11/1975 | Kwiatkowski . |
| 3,925,324 | 12/1975 | Gerard . |
| 3,933,862 | 1/1976 | Williams, III . |
| 3,935,167 | 1/1976 | Marvel et al. . |
| 3,935,320 | 1/1976 | Chiu et al. . |
| 3,941,746 | 3/1976 | Stephen . |
| 3,956,320 | 5/1976 | Heath et al. . |
| 3,957,732 | 5/1976 | Hirooka et al. . |
| 3,957,862 | 5/1976 | Heath et al. . |
| 3,966,678 | 6/1976 | Gruffaz et al. . |
| 3,966,726 | 6/1976 | Toth et al. . |
| 3,966,749 | 6/1976 | Bodor et al. . |
| 3,966,987 | 6/1976 | Suzuki et al. . |
| 3,970,714 | 7/1976 | Bargain . |
| 3,972,902 | 8/1976 | Heath et al. . |
| 3,988,374 | 10/1976 | Brode et al. . |
| 3,993,630 | 11/1976 | Darmory et al. . |
| 3,998,786 | 12/1976 | D'Alelio . |
| 4,000,146 | 12/1976 | Gerber . |
| 4,005,134 | 1/1977 | Markezich . |
| 4,013,600 | 3/1977 | Cassat . |
| 4,020,069 | 4/1977 | Johnson et al. . |
| 4,026,871 | 5/1977 | D'Alelio . |
| 4,038,261 | 7/1977 | Crouch et al. . |
| 4,051,177 | 9/1977 | Braden et al. . |
| 4,055,543 | 10/1977 | D'Alelio . |
| 4,058,505 | 11/1977 | D'Alelio . |
| 4,060,515 | 11/1977 | D'Alelio . |
| 4,064,289 | 12/1977 | Yokoyama et al. . |
| 4,075,171 | 2/1978 | D'Alelio . |
| 4,097,456 | 6/1978 | Barie . |
| 4,100,137 | 7/1978 | Lemieux et al. . |
| 4,100,138 | 7/1978 | Bilow et al. . |
| 4,101,488 | 7/1978 | Ishizuka et al. . |
| 4,107,147 | 8/1978 | Williams, III et al. . |
| 4,107,153 | 8/1978 | Akijama et al. . |
| 4,107,174 | 8/1978 | Baumann et al. . |
| 4,108,837 | 8/1978 | Johnson et al. . |
| 4,108,926 | 8/1978 | Arnold et al. . |
| 4,111,879 | 9/1978 | Mori et al. . |
| 4,115,231 | 9/1978 | Darms et al. . |
| 4,115,362 | 9/1978 | Inata et al. . |
| 4,116,937 | 9/1978 | Jones et al. . |
| 4,124,593 | 11/1978 | Gschwend et al. . |
| 4,126,619 | 11/1978 | Darms et al. . |
| 4,128,574 | 12/1978 | Markezich et al. . |
| 4,132,715 | 1/1979 | Roth . |
| 4,132,716 | 1/1979 | Kvita et al. . |
| 4,134,895 | 1/1979 | Roth et al. . |
| 4,142,870 | 3/1979 | Lovejoy . |
| 4,158,731 | 6/1979 | Baumann et al. . |
| 4,166,168 | 8/1979 | D'Alelio . |
| 4,167,663 | 9/1979 | Granzow et al. . |
| 4,168,366 | 9/1979 | D'Alelio . |
| 4,172,836 | 10/1979 | Baumann et al. . |
| 4,174,326 | 11/1979 | Baumann et al. . |
| 4,175,175 | 11/1979 | Johnson et al. . |
| 4,176,223 | 11/1979 | Irwin . |
| 4,179,551 | 12/1979 | Jones et al. . |
| 4,183,839 | 1/1980 | Gagliani . |
| 4,187,364 | 2/1980 | Darms et al. . |
| 4,189,560 | 2/1980 | Roth et al. . |
| 4,193,927 | 3/1980 | Baumann et al. . |
| 4,197,397 | 4/1980 | D'Alelio . |
| 4,200,731 | 4/1980 | Massey et al. . |
| 4,206,106 | 6/1980 | Heilman et al. . |
| 4,218,555 | 8/1980 | Antonoplos et al. . |
| 4,221,895 | 9/1980 | Woo . |
| 4,225,497 | 9/1980 | Baudouin et al. . |
| 4,225,498 | 9/1980 | Baudouin et al. . |
| 4,231,934 | 11/1980 | Oba et al. . |
| 4,234,712 | 11/1980 | Keller et al. . |
| 4,237,262 | 12/1980 | Jones . |
| 4,239,883 | 12/1980 | Stenzenberger . |
| 4,244,853 | 1/1981 | Serafini et al. . |

| | | |
|---|---|---|
| 4,250,096 | 2/1981 | Kvita et al. . |
| 4,251,417 | 2/1981 | Chow et al. . |
| 4,251,418 | 2/1981 | Chow et al. . |
| 4,251,419 | 2/1981 | Heilman et al. . |
| 4,251,420 | 2/1981 | Antonoplos et al. . |
| 4,251,918 | 2/1981 | Chow et al. . |
| 4,255,313 | 3/1981 | Antonoplos et al. . |
| 4,266,047 | 5/1981 | Jablonski et al. . |
| 4,269,961 | 5/1981 | Jones et al. . |
| 4,271,079 | 6/1981 | Maeda et al. . |
| 4,273,916 | 6/1981 | Jones . |
| 4,276,407 | 6/1981 | Bilow et al. . |
| 4,288,583 | 9/1981 | Zahir et al. . |
| 4,288,607 | 9/1981 | Bier et al. . |
| 4,289,699 | 9/1981 | Oba et al. . |
| 4,293,670 | 10/1981 | Robeson et al. . |
| 4,297,472 | 10/1981 | Heiss . |
| 4,297,474 | 10/1981 | Williams, III et al. . |
| 4,298,720 | 11/1981 | Yamazaki et al. . |
| 4,299,750 | 11/1981 | Antonoplos et al. . |
| 4,299,946 | 11/1981 | Balme et al. . |
| 4,302,575 | 11/1981 | Takekoshi . |
| 4,323,662 | 4/1982 | Oba et al. . |
| 4,338,222 | 7/1982 | Limburg et al. . |
| 4,338,225 | 7/1982 | Sheppard . |
| 4,344,869 | 8/1982 | Blinne et al. . |
| 4,344,870 | 8/1982 | Blinne et al. . |
| 4,351,932 | 9/1982 | Street et al. . |
| 4,358,561 | 11/1982 | Keske et al. . |
| 4,360,644 | 11/1982 | Naarmann et al. . |
| 4,365,068 | 12/1982 | Darms et al. . |
| 4,375,427 | 3/1983 | Miller et al. . |
| 4,376,710 | 3/1983 | Gardos et al. . |
| 4,381,363 | 4/1983 | Reinhart, Jr. . |
| 4,389,504 | 6/1983 | St. Clair et al. . |
| 4,393,188 | 7/1983 | Takahashi et al. . |
| 4,395,497 | 7/1983 | Naarmann et al. . |
| 4,400,613 | 8/1983 | Popelish . |
| 4,405,770 | 9/1983 | Schoenberg et al. . |
| 4,407,739 | 10/1983 | Naarmann et al. . |
| 4,409,382 | 10/1983 | Keller . |
| 4,410,686 | 10/1983 | Hefner, Jr. et al. . |
| 4,414,269 | 11/1983 | Lubowitz et al. . |
| 4,417,039 | 11/1983 | Reinhardt et al. . |
| 4,417,044 | 11/1983 | Parekh . |
| 4,418,181 | 11/1983 | Monacelli . |
| 4,423,202 | 12/1983 | Choe . |
| 4,429,108 | 1/1984 | Stephens . |
| 4,438,273 | 3/1984 | Landis . |
| 4,438,280 | 3/1984 | Monacelli . |
| 4,446,191 | 5/1984 | Miyadera et al. . |
| 4,448,925 | 5/1984 | Hanson . |
| 4,460,783 | 7/1984 | Nishikawa et al. . |
| 4,465,809 | 8/1984 | Smith . |
| 4,467,011 | 8/1984 | Brooks et al. . |
| 4,476,184 | 10/1984 | Lubowitz et al. . |
| 4,476,295 | 10/1984 | Stephens . |
| 4,482,683 | 11/1984 | Quella et al. . |
| 4,485,140 | 11/1988 | Gannett et al. . |
| 4,485,231 | 11/1984 | Landis . |
| 4,489,027 | 12/1984 | St. Clair et al. . |
| 4,504,632 | 3/1985 | Holub et al. . |
| 4,507,466 | 3/1985 | Tomalia et al. . |
| 4,510,272 | 4/1985 | Loszewski . |
| 4,515,962 | 5/1985 | Renner . |
| 4,519,926 | 5/1985 | Basalay et al. . |
| 4,520,198 | 5/1985 | D'Alelio et al. . |
| 4,526,838 | 7/1985 | Fujioka et al. . |
| 4,533,692 | 8/1985 | Wolfe et al. . |
| 4,533,693 | 8/1985 | Wolfe et al. . |
| 4,533,724 | 8/1985 | Wolfe et al. . |
| 4,535,117 | 8/1985 | Mathis et al. . |
| 4,536,559 | 8/1985 | Lubowitz et al. . |
| 4,542,203 | 9/1985 | Ueno et al. ............ 528/176 |
| 4,547,553 | 10/1985 | Lubowitz et al. . |
| 4,555,563 | 11/1985 | Hefner, Jr. et al. . |
| 4,556,697 | 12/1985 | Curatolo et al. . |
| 4,556,705 | 12/1985 | McCready . |
| 4,558,120 | 12/1985 | Tomalia et al. . |
| 4,562,231 | 12/1985 | Dean . |
| 4,562,232 | 12/1985 | Smith . |
| 4,563,498 | 1/1986 | Lucas . |
| 4,563,514 | 1/1986 | Liu et al. . |
| 4,564,553 | 1/1988 | Pellegrini et al. . |
| 4,567,216 | 1/1986 | Qureshi et al. . |
| 4,567,240 | 1/1986 | Hergenrother et al. . |
| 4,568,737 | 2/1986 | Tomalia et al. . |
| 4,574,144 | 3/1986 | Yates, III et al. . |
| 4,574,148 | 3/1986 | Wicker, Jr. et al. . |
| 4,574,154 | 3/1986 | Okamoto et al. . |
| 4,576,857 | 3/1986 | Gannett et al. . |
| 4,577,034 | 3/1986 | Durvasula . |
| 4,578,433 | 3/1986 | Muenstedt et al. . |
| 4,578,470 | 3/1986 | Webb . |
| 4,584,364 | 4/1986 | Lubowitz et al. . |
| 4,587,329 | 5/1986 | Tomalia et al. . |
| 4,590,363 | 5/1986 | Bernard . |
| 4,599,383 | 7/1986 | Satoji . |
| 4,600,769 | 7/1986 | Kumar et al. . |
| 4,604,437 | 8/1986 | Renner . |
| 4,608,414 | 8/1986 | Kitsunai et al. . |
| 4,608,426 | 8/1986 | Stern . |
| 4,611,022 | 9/1986 | Hefner, Jr. . |
| 4,611,048 | 9/1986 | Peters . |
| 4,614,767 | 9/1986 | Dean . |
| 4,615,832 | 10/1986 | Kress et al. . |
| 4,616,070 | 10/1986 | Zeiner et al. . |
| 4,616,071 | 10/1986 | Holubka . |
| 4,617,390 | 10/1986 | Hoppe et al. . |
| 4,624,725 | 11/1986 | Lamm et al. . |
| 4,624,888 | 11/1986 | St. Clair et al. . |
| 4,628,067 | 12/1986 | Chen, Sr. et al. . |
| 4,628,079 | 12/1986 | Zecher et al. . |
| 4,629,777 | 12/1986 | Pfeifer . |
| 4,631,337 | 12/1986 | Tomalia et al. . |
| 4,638,027 | 1/1987 | Mark et al. . |
| 4,640,944 | 2/1987 | Brooks . |
| 4,649,080 | 3/1987 | Fischer et al. . |
| 4,654,410 | 3/1987 | Kashiwame et al. . |
| 4,657,973 | 4/1987 | Endo et al. . |
| 4,657,977 | 4/1987 | Peters . |
| 4,657,987 | 4/1987 | Rock et al. . |
| 4,657,990 | 4/1987 | Daoust et al. . |
| 4,660,057 | 4/1987 | Watanabe et al. . |
| 4,661,604 | 4/1987 | Lubowitz et al. . |
| 4,663,378 | 5/1987 | Allen . |
| 4,663,399 | 5/1987 | Peters . |
| 4,663,423 | 5/1987 | Yamada et al. . |
| 4,663,424 | 5/1987 | Stix et al. . |
| 4,663,425 | 5/1987 | Evers et al. . |
| 4,680,326 | 7/1987 | Leland et al. . |
| 4,680,377 | 7/1987 | Matsumura et al. . |
| 4,684,714 | 8/1987 | Lubowitz et al. . |
| 4,690,972 | 9/1987 | Johnson et al. . |
| 4,691,025 | 9/1987 | Domeier et al. . |
| 4,694,064 | 9/1987 | Tomalia et al. . |
| 4,695,610 | 9/1987 | Egli et al. . |
| 4,699,975 | 10/1987 | Katto et al. . |
| 4,703,081 | 10/1987 | Blackwell et al. . |
| 4,708,983 | 11/1987 | Liang . |
| 4,709,004 | 11/1987 | Dai . |
| 4,709,006 | 11/1987 | Tsai et al. . |
| 4,709,008 | 11/1987 | Shimp . |
| 4,714,768 | 12/1987 | Hemkielm et al. . |

| | | |
|---|---|---|
| 4,716,212 | 12/1987 | Gaughan . |
| 4,719,283 | 1/1988 | Bartmann . |
| 4,727,118 | 2/1988 | Egami . |
| 4,728,742 | 3/1988 | Renner . |
| 4,730,030 | 3/1988 | Hahn et al. . |
| 4,737,550 | 4/1988 | Tomalia . |
| 4,739,030 | 4/1988 | Lubowitz et al. . |
| 4,739,075 | 4/1988 | Odagiri et al. . |
| 4,739,115 | 4/1988 | Byrd et al. . |
| 4,740,563 | 4/1988 | McCready et al. . |
| 4,740,564 | 4/1988 | McCready et al. . |
| 4,740,584 | 4/1988 | Shimp . |
| 4,742,166 | 5/1988 | Renner . |
| 4,748,227 | 5/1988 | Matzner et al. . |
| 4,755,584 | 7/1988 | Tomioka et al. . |
| 4,755,585 | 7/1988 | Hanson et al. . |
| 4,757,118 | 7/1988 | Das et al. . |
| 4,757,128 | 7/1988 | Domb et al. . |
| 4,757,150 | 7/1988 | Guggenheim et al. . |
| 4,759,986 | 7/1988 | Marikar et al. . |
| 4,760,106 | 7/1988 | Garnder et al. . |
| 4,764,427 | 8/1988 | Hara et al. . |
| 4,766,180 | 8/1988 | Wong . |
| 4,766,197 | 8/1988 | Clendinning et al. . |
| 4,769,424 | 9/1988 | Takekoshi et al. . |
| 4,769,426 | 9/1988 | Iwasaki et al. . |
| 4,769,436 | 9/1988 | Beck et al. . |
| 4,774,282 | 9/1988 | Qureshi . |
| 4,777,208 | 10/1988 | Hefner, Jr. . |
| 4,778,830 | 10/1988 | Streu et al. . |
| 4,778,859 | 10/1988 | Ai et al. . |
| 4,778,898 | 10/1988 | Vonlanthen et al. . |
| 4,786,669 | 11/1988 | Dewhirst . |
| 4,786,685 | 11/1988 | Takida et al. . |
| 4,786,713 | 11/1988 | Rule et al. . |
| 4,798,685 | 1/1989 | Yaniger . |
| 4,798,686 | 1/1989 | Hocker et al. . |
| 4,798,882 | 1/1989 | Petri . |
| 4,801,676 | 1/1989 | Hisgen et al. . |
| 4,801,677 | 1/1989 | Eckhardt et al. . |
| 4,804,722 | 2/1989 | Hesse et al. . |
| 4,804,724 | 2/1989 | Harris et al. . |
| 4,806,407 | 2/1989 | Skinner et al. . |
| 4,808,717 | 2/1989 | Saito et al. . |
| 4,812,518 | 3/1989 | Haubennestel et al. . |
| 4,812,534 | 3/1989 | Blakely . |
| 4,812,552 | 3/1989 | Cliffton et al. . |
| 4,812,588 | 3/1989 | Schrock . |
| 4,814,416 | 3/1989 | Poll . |
| 4,814,417 | 3/1989 | Sugimori . |
| 4,814,421 | 3/1989 | Rosenquist . |
| 4,814,472 | 3/1989 | Lau . |
| 4,816,503 | 3/1989 | Cunningham et al. . |
| 4,816,526 | 3/1989 | Bristowe et al. . |
| 4,816,527 | 3/1989 | Rock . |
| 4,816,556 | 3/1989 | Gay et al. . |
| 4,820,770 | 4/1989 | Schleifstein . |
| 4,826,927 | 5/1989 | Schmid et al. . |
| 4,826,997 | 5/1989 | Kirchhoff . |
| 4,827,000 | 5/1989 | Schwartz . |
| 4,829,138 | 5/1989 | Barthelemy . |
| 4,835,197 | 5/1989 | Mercer . |
| 4,837,256 | 6/1989 | Gardner et al. . |
| 4,839,378 | 6/1989 | Koyama et al. . |
| 4,845,150 | 7/1989 | Kovak et al. . |
| 4,845,167 | 7/1989 | Alston et al. . |
| 4,845,185 | 7/1989 | Teramoto et al. . |
| 4,845,278 | 7/1989 | Erhan . |
| 4,847,333 | 7/1989 | Lubowitz et al. . |
| 4,851,280 | 7/1989 | Gupta . |
| 4,851,287 | 7/1989 | Hartsing, Jr. . |
| 4,851,494 | 7/1989 | Eldin et al. . |
| 4,851,495 | 7/1989 | Sheppard et al. . |
| 4,851,496 | 7/1989 | Poll et al. . |
| 4,851,501 | 7/1989 | Lubowitz et al. . |
| 4,851,505 | 7/1989 | Hayes . |
| 4,861,855 | 8/1989 | Bockrath et al. . |
| 4,861,882 | 8/1989 | Hergenrother et al. . |
| 4,861,915 | 8/1989 | Clendinning et al. . |
| 4,861,924 | 8/1989 | Riggs . |
| 4,868,270 | 9/1989 | Lubowitz et al. . |
| 4,871,475 | 10/1989 | Lubowitz et al. . |
| 4,874,834 | 10/1989 | Higashi et al. . |
| 4,876,325 | 10/1989 | Olson et al. . |
| 4,876,328 | 10/1989 | Lubowitz et al. . |
| 4,876,330 | 10/1989 | Higashi et al. . |
| 4,891,167 | 1/1990 | Clendinning et al. . |
| 4,891,408 | 1/1990 | Newman-Evans . |
| 4,891,460 | 1/1990 | Ishii . |
| 4,895,892 | 1/1990 | Satake et al. . |
| 4,895,924 | 1/1990 | Satake et al. . |
| 4,897,527 | 1/1990 | Cripps et al. . |
| 4,902,335 | 2/1990 | Kume et al. . |
| 4,902,440 | 2/1990 | Takeyama et al. . |
| 4,902,769 | 2/1990 | Cassidy et al. . |
| 4,902,773 | 2/1990 | Bodnar et al. . |
| 4,909,382 | 3/1990 | Keller . |
| 4,916,210 | 4/1990 | Jackson . |
| 4,916,235 | 4/1990 | Tan et al. . |
| 4,919,992 | 4/1990 | Blundell et al. . |
| 4,923,752 | 5/1990 | Cornelia . |
| 4,927,899 | 5/1990 | Michaud et al. . |
| 4,927,900 | 5/1990 | Michaud et al. . |
| 4,931,531 | 6/1990 | Tamai et al. . |
| 4,931,540 | 6/1990 | Mueller et al. . |
| 4,935,523 | 6/1990 | Lubowitz et al. . |
| 4,958,031 | 9/1990 | Sheppard et al. . |
| 4,960,835 | 10/1990 | Towle et al. . |
| 4,965,336 | 10/1990 | Lubowitz et al. . |
| 4,973,662 | 11/1990 | Odagiri et al. . |
| 4,980,481 | 12/1990 | Lubowitz et al. . |
| 4,981,922 | 1/1991 | Sheppard et al. . |
| 4,985,568 | 1/1991 | Lubowitz et al. . |
| 4,990,624 | 2/1991 | Sheppard et al. . |
| 4,996,101 | 2/1991 | Landis et al. . |
| 5,003,035 | 3/1991 | Tsai et al. . |
| 5,011,905 | 4/1991 | Lubowitz et al. . |
| 5,066,541 | 11/1991 | Lubowitz et al. . |
| 5,066,776 | 11/1991 | Russeler et al. . |
| 5,071,941 | 12/1991 | Lubowitz et al. . |
| 5,075,537 | 12/1991 | Lorenzen et al. . |
| 5,082,905 | 1/1992 | Lubowitz et al. . |
| 5,086,154 | 2/1992 | Camberlin et al. . |
| 5,087,701 | 2/1992 | Lubowitz et al. . |
| 5,104,967 | 4/1992 | Sheppard et al. . |
| 5,109,105 | 4/1992 | Lubowitz et al. . |
| 5,111,026 | 5/1992 | Ma . |
| 5,112,936 | 5/1992 | Okamoto . |
| 5,112,939 | 5/1992 | Lubowitz et al. . |
| 5,115,087 | 5/1992 | Sheppard et al. . |
| 5,116,935 | 5/1992 | Lubowitz et al. . |
| 5,120,819 | 6/1992 | Lubowitz et al. . |
| 5,126,410 | 6/1992 | Lubowitz et al. . |
| 5,144,000 | 9/1992 | Sheppard et al. . |
| 5,151,487 | 9/1992 | Lubowitz et al. . |
| 5,155,206 | 10/1992 | Lubowitz et al. . |
| 5,159,055 | 10/1992 | Sheppard et al. . |
| 5,175,233 | 12/1992 | Lubowitz et al. ........................ 528/170 |
| 5,175,234 | 12/1992 | Lubowitz et al. . |
| 5,175,304 | 12/1992 | Sheppard . |
| 5,198,526 | 3/1993 | Lubowitz et al. . |
| 5,210,213 | 5/1993 | Sheppard et al. ........................ 548/435 |
| 5,216,117 | 6/1993 | Sheppard et al. . |
| 5,227,461 | 7/1993 | Lubowitz et al. . |

| | | |
|---|---|---|
| 5,230,956 | 7/1993 | Cole et al. . |
| 5,239,046 | 8/1993 | Lubowitz et al. . |
| 5,254,605 | 10/1993 | Kim et al. . |
| 5,268,519 | 12/1993 | Sheppard et al. . |
| 5,286,811 | 2/1994 | Lubowitz et al. . |
| 5,338,532 | 8/1994 | Tomalia et al. . |
| 5,344,894 | 9/1994 | Lubowitz . |
| 5,403,666 | 4/1995 | Lubowitz et al. ............... 428/474.4 |

FOREIGN PATENT DOCUMENTS

| | | |
|---|---|---|
| 7100975 | 1/1971 | France . |
| 2166209 | 8/1973 | France . |
| 2210635 | 7/1974 | France . |
| 2272119 | 12/1975 | France . |
| 2303818 | 10/1976 | France . |
| 1951632 | 5/1971 | Germany . |
| 1453625 | 12/1973 | Japan . |
| 58-059219 | 10/1981 | Japan . |
| 1210408A | 2/1988 | Japan . |
| 907105 | 10/1962 | United Kingdom . |
| 1069061 | 5/1967 | United Kingdom . |
| 1099096 | 1/1968 | United Kingdom . |
| 1453625 | 10/1976 | United Kingdom . |
| 2002378 | 2/1977 | United Kingdom . |
| 2002378 | 2/1979 | United Kingdom . |
| 2002378 | 3/1982 | United Kingdom . |
| 81/01855 | 7/1981 | WIPO . |
| 84/04313 | 11/1984 | WIPO . |

OTHER PUBLICATIONS

Spillman et al., *Copolymers of Poly(Para–Phenylene Terephthalamide) Containing a Thermally Activated Cross–Linking Agent* PMSE vol. 68, Spring Meetings 139–140, 1993.

Radlmann, et al., *New Synthesis of Poly(ether Ketones)*. (44195h), Chem. Abstracts vol. 72, 1970, p. 44187, 1970.

Bryant et al., *Synthesis and Properties of Phenylethynyl––Terminated Polyimides* Polymer PrePrints, vol. 34, No. 1, 566–567, Mar. 1993.

Crivello et al., *Polyimidothioether–Polysulfide Block Polymers* Polymer Sci., Polymer Chem., Ed., vol. 13, pp. 1819–1842, 1975.

Frazer, *High Temperature Resistant Polymers* Interscience Publishers, John Wiley & Sons, Inc., 139–213, 1968.

Mittal (ed), *Polyimides* Plenum Press, NY, vol. 1 & 2 (selected pages) Publication Date Unavail.

St. Clair et al., *The Development of Aerospace Polyimide Adhesives* Mittal (ed), Polyimides–Synthesis Characterization and Applications, Plenum Press, NY, vol. 2, pp. 977–1041, 1973.

Serafini, et al., *A Review of Processable High Temperature Resistant Addition–type Laminating Resins*, Mittal (ed), Polyimides–Synthesis, Characterization and Applications, Plenum Press, NY, vol. 1, pp. 89–95, 1973.

Stenson, *Polycyanurates Find Applications; Their Chemistry Remains Puzzling* Science/Technology, 208 ACS National Meeting, Washington, D.C., C&EN Northeast News Bureau 30–31, Sep. 1994.

Sutter, et al., *Easily Processable High–Temperature Polyimide* NASA Tech. Briefs (two pages).

Stoakley, et al., *Low–Dielectric–Constant Polyimides/Glass Composites* NASA Tech. Briefs p. 24, Apr. 1994.

Bartolotta, *Predicting Fatigue Lives of Metal–Matrix/Fiber Composites* NASA Tech Briefs pp. 28, 30, Apr. 1994.

Vannucci, et al., *Improved PMR Polyimides for Heat–Stable Laminates* NASA Tech Briefs pp. 30–31, Apr. 1994.

Bryant, et al., *Phenylethynyl End–Capping Reagents and Reactive Diluents* NASA Tech Briefs pp. 36–37, Apr. 1994.

Jensen, et al., *Phenylethynyl–Terminated Ploy(Arylene Ethers)*, NASA Tech Briefs p. 37, Apr. 1994.

Buckley, et al., *Processable Polyimides for High Temperature Applications*, 36th International SAMPE Symposium pp. 1172–1181, Apr. 1991.

Edwards, et al. *Constituents of the Higher Fungi. Part XII.[1] 2–Aryl–3–methoxymaleic Anhydrides from Pulvinic Acid Derivatives. A Convenient Method for Determination of Structure of Fungaland Lichen Pulvinic Acid Derivatives*, Journal of The Chemical Society pp. 1538–1542, 1973.

Morrison, et al., *"Reactions" and Hofmann degradation of amides* Organic Chemistry Second Edition pp. 591 and 735, Publication Date Unavailable.

Kwiatkowski, et al., *Thermosetting Diphenyl Sulfone–Based Malcimides* Journal of Polymer Science, vol. 13, pp. 961–972, 1975.

Lyle et al., *Polyarylene Ethers: Maleimides, Nadimides and Blends* the Interdisciplinary Symposium on Recent Advances in Polyimides and Other High Performance Polymers, San Diego, California pp. K–1–K–7, Jan. 1990.

Roberts et al., *Effect of Solution Concentration and Aging Conditions on PMR–15 Resin* SAMPE Journal, pp. 24–28, 213, Mar./Apr. 1986.

Southcott, et al., "The Development of Processable, Fully Imidized, Polyimides for High–Temperature Applications", High Perform. Polym. 6, pp. 1–12, Printed in UK, 1994.

Vinogradova et al., Chemical Abstract 67:100458, Vysokomol. Soedin., Ser A (1967) 9(8) 1797–801.

Vinogradova et al., Vysokomol. Soedin., Ser. A (1967) 9(8), 1797–801.

Sheppard, et al., "Advanced Thermoplastic Composite Development", 38th Annual Conference, Reinforced Plastics Composites Instituet, The Society of the Plastic Industry Inc., Feb. 16–20, 1981.

Jaquish, et al., "Graphite Reinforced Thermoplastic Composites", Final Report on Contract N00019–79–C 0203, Boeing Aerospace Company, Seattle, Washington, 98124, Aug. 1980.

THALLIUM CATALYZED MULTIDIMENSIONAL ESTER OLIGOMERS

REFERENCE TO RELATED APPLICATIONS

The present application is a divisional application based upon U.S. patent application Ser. No. 07/176,518, filed Apr. 1, 1988, which was a continuation-in-part application based upon U.S. patent application 06/810,817, filed Dec. 17, 1985, now abandoned which was a continuation-in-part application based upon U.S. patent application 06/726,258, filed Apr. 23, 1985, now abandoned.

TECHNICAL FIELD

The present invention relates to multidimensional polyesters made using thallium ethoxide as a catalyst.

BACKGROUND OF THE INVENTION

In our earlier applications we proposed the condensation of hydroxyl (—OH) and carboxylic acid (—COOH) or carboxylic acid halides (—COX) on an aromatic hub having at least three such functionalities. The condensation occurred in a suitable solvent, such as DMAC, under an inert atmosphere in the presence of triethylamine (TEA). We have found that, when reacting, for example, phloroglucinol with an acid chloride end cap of the formula:

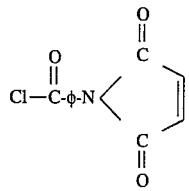

in DMAC and TEA that the resulting product is a mixture

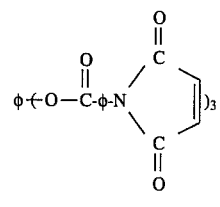

(I)

and

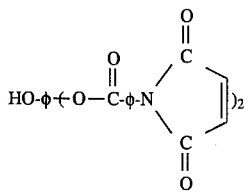

(II)

The condensation is difficult to drive to completion (i.e., replacement of all the —OH groups) to yield the desired product (I). The yield of fully reacted multidimensional ester (I) can be improved, however, by replacing the TEA with thallium ethoxide (Tl—OC$_2$H$_5$).

SUMMARY OF THE INVENTION

The present invention relates to fully substituted, multidimensional polyester oligomers made using thallium catalysts, particularly thallium ethoxide. These multidimensional polyesters are obtainable by reacting a compound of the formula: Ar—(—Q)$_w$ wherein Ar is an aromatic radical of valency w;
w is a small integer greater than or equal to 3;
Q is ⁻OH or ⁻COX; and
X is halogen
with a compound of the formula:
ρ—P wherein
ρ is a hydrocarbon radical; and
P is ⁻OH if Q is ⁻COX and is ⁻COX if Q is ⁻OH Generally, the solvent is DMAC or a mixture of DMAC with other suitable solvents. Ar—(—Q)$_w$ typically is phloroglucinol, in which case ρ—P is an acid halide where ρ has the formula: D$_i$—φ— wherein i is 1 or 2;
φ is phenylene;
D is an unsaturated hydrocarbon radical that generally includes a segment selected from the group consisting of:

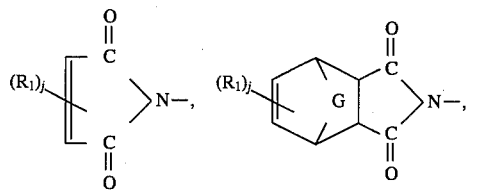

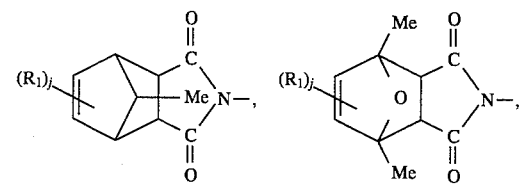

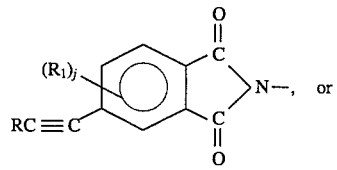

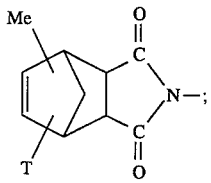

$R_1$ is lower alkyl, aryl, substituted alkyl, substituted aryl, lower alkoxy, aryloxy, halogen, or mixtures thereof;
G is —O—, —S—, —₂—, —CH$_2$—, —CO—, —CHR—, —SO—, or —C(R)$_2$;
j is 0, 1, or 2
T is allyl or methallyl;
Me is methyl; and
R is hydrogen, lower alkyl, or phenyl.

Extending polyester oligomers that are fully substituted because of the thallium catalysis can be made by reacting Ar—(—Q)$_w$ with a dibasic carboxylic acid or a diol of the formula ρ—(—P)$_2$ wherein ρ is a divalent hydrocarbon radical, especially a phenoyphenyl sulfone, and P is —COX. In this case, the reaction vessel also is changed with an end cap, typically of the formula: D$_i$—φ—Q wherein D, I, φ, and Q are previously defined.

The multidimensional polyester oligomers that result from the reaction are esters or alternating esters of the formula:

Ar—(—OOC—ρ)$_w$;

Ar—(—COO—ρ)$_w$;

Ar—(—OOC—ρ—COO—φ—D$_i$)$_w$; or

Ar—(—COO—ρ—OOC—φ—D$_i$)$_w$.

Best Mode Contemplated for the Present Invention

The yield of multidimensional polyesters can be improved by replacing triethylamine (TEA) in the condensation solution with thallium ethoxide (Tl—OC$_2$H$_5$) as a catalyst. Since the polyester oligomers that are synthesized are often used without isolation of products, we believe that the new product, richer in product (I) [i.e. the truly multidimensional ester) will yield better composites than are achieved with the multidimensional (I) and linear (II) blend made using TEA as a catalyst.

The method of the present invention is equally applicable to use of an acid halide hub such as cyuranic acid chloride with a mono- or difunctional imidophenyl end cap monomer. Chain-extension can be achieved, also, by including dialcohols, diacid halides, or both in the condensation mixture.

We believe that Tl—OC$_2$H$_5$ will produce a higher yield of the tri-substituted hub. If the hub has more than three reactive hydroxyl or acid halide functionalities, the thallium ethoxide catalyst will promote more complete reaction (or substitution) than TEA.

While thallium ethoxide is preferred, it is possible that any lower alkoxy substituent on the metal will be active as a catalyst. That is, methoxy, propoxy, isopropoxy, n-butoxy, phenoxy, or the like may also display catalytic activity.

Accordingly, the present invention relates to the catalysis of the —OH/—COX or —OH/—COOH condensation with a thallium catalyst, and, particularly, to the preparation of multidimensional polyesters by the condensation of Ar—(Q)$_w$ with a corresponding alcohol (—OH), acid (—COOH), or acid halide (—COX) in a suitable solvent under an inert atmosphere with or without heating in the presence of thallium ethoxide, wherein Ar=an aromatic radical of valency w;

w=an integer greater than or equal to 3; and

Q=—OH, —COOH, or —COX.

The aromatic radical will generally be phenyl or azalinyl, being the residue, for example of phloroglucinol or cyranic acid chloride. Those compounds described in U.S. Pat. Nos. 4,617,390 or 4,709,008 may also be used as hubs, and amine compounds can be reacted with an acid anhydride to form polycarboxylic acids that are suitable hubs. Triaminobenzene or the polyamines of U.S. Pat. No. 4,574,152 are suitable reactants (precursors) in this context.

The simplest oligomers can be prepared by condensing about 1 mole of the hub with a crosslinking end cap monomer of the formula:

D$_i$—φ—P wherein

φ=phenyl;

P=—COX, if the hub is a polyol, or —OH, if the hub is a polybasic acid;

i=1 or 2;

D=an unsaturated hydrocarbon radical that generally includes a segment selected from the group consisting of:

R$_1$=lower alkyl, aryl, substituted alkyl, substituted aryl, lower alkoxy, aryloxy, halogen, or mixtures thereof;

G=—O—, —S—, —SO$_2$—, —CH$_2$—, —CO—, —CHR—, —SO—, or —CR$_2$—;

j=0, 1, or 2;

T=allyl or methallyl;

Me=methyl; and

R=hydrogen, lower alkyl, or phenyl.

These end cap monomers allow the multidimensional polyester oligomers to be cured into high performance, advanced composites that have use temperature that exceed (often substantially) their curing temperatures.

The arms of the multidimensional oligomers can be extended if the reaction solution's components are adjusted. For example, the hub of the formula Ar—(Q)$_w$ can be simultaneously condensed with R—(P)$_2$ wherein Ar=an aromatic radical of valency w;

w=a small integer greater than or equal to 3;

Q=—COX, —OH, or —COOH;

R=a divalent hydrocarbon radical, especially a phenoxyphenylsulfone; and

P=—OH, if Q=—COX or —COOH, or —COX or —COOH, if Q=—OH with a crosslinking end cap monomer of the formula:

D$_i$—φ—Q wherein D, i, φ, or Q are as previously defined.

The dialcohols or diacid halides include those compounds disclosed in U.S. Pat. No. 4,547,553 or in our copending applications.

The reaction solution may include four or more component mixtures but deleterious or interfering competitive reactions are likely to occur, dictating staged reaction rather than simultaneous condensation. For example, Ar—(Q)$_w$ can be condensed with R—(P)$_2$ followed by addition of $R_1$—(Q)$_2$ and $D_i$—ϕ—P to form a multidimensional polyester having extended arms (i.e., arms of relatively high average formula weight).

While preferred embodiments have been described, those skilled in the art will readily recognize alterations, variations, or modifications which might be made to the embodiments without departing from the inventive concept. Therefore, the claims should be interpreted liberally with the support of the full range of equivalents known to those of ordinary skill based upon this description. The claims should be limited only as is necessary in view of the pertinent prior art.

We claim:

1. A multidimensional polyester composition as produced prior to isolation of the polyester obtainable by reacting substantially stoichiometric amounts of a compound of the formula Ar—(—Q)$_w$ wherein Ar=an aromatic radical of valency w;

w=a small integer greater than or equal to 3;

Q=—OH or —COX; and

X=halogen with a compound of the formula ρ—P wherein

ρ   =   a hydrocarbon radical; and
P   =   —OH, if Q = —COX; and
       —COX, if Q = —OH in a suitable solvent under an inert atmosphere in the presence of an effective amount of a thallium catalyst, the polyester being Ar—{COO—ρ}$_w$ or Ar—{OOC—ρ}$_w$.

2. The polyester composition of claim 1 wherein the catalyst is thallium ethoxide.

3. The polyester composition of claim 1 wherein Ar(—Q)$_w$ is phloroglucinol.

4. The polyester composition of claim 1 wherein Ar is phenylene and w is 3.

5. A polyester obtainable by reacting ϕ—(OH)$_3$, XOC—ρ—COX, and D$_i$—ϕ—OH in substantially stoichiometric proportions in a suitable solvent in the presence of a thallium catalyst to achieve substantially complete substitution of the XOC—ρ—COX compound on the ϕ—(OH)$_3$ to yield the product ϕ—(OOC—ρCOO—)ϕ—D$_i$ wherein i is 1 or 2;

ϕ is phenylene;

D is selected from the group consisting of:

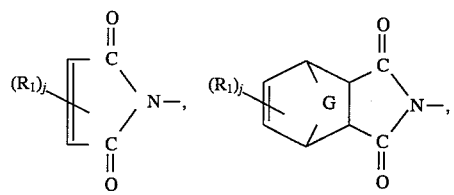

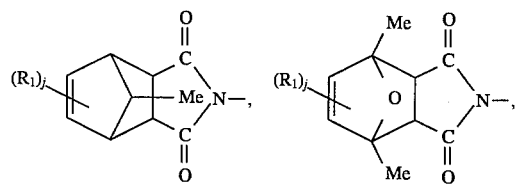

-continued

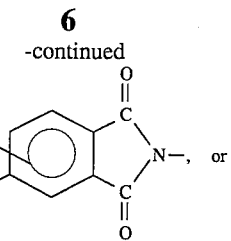

$R_1$ is lower alkyl, aryl, substituted alkyl, substituted aryl, lower alkoxy, aryloxy, halogen, or mixtures thereof;

G is —O—, —S—, —SO$_2$—, —CH$_2$—, —CO—, —CHR—, —SO—, or —C(R)$_2$—;

j is 0, 1, or 2;

T is allyl or methallyl;

Me is methyl;

R is hydrogen, lower alkyl, or phenyl; and

ρ is a divalent hydrocarbon radical.

6. A multidimensional polyester obtainable by reacting substantially stoichiometric amounts of a compound of the formula Ar—(Q)$_w$ wherein Ar=an aromatic radical of valency w;

w=a small integer greater than or equal to 3;

Q=—OH or —COX; and

X=halogen with a compound of the formula ρ—P wherein

ρ   =   a hydrocarbon radical; and
P   =   —OH, if Q = —COX; and
       —COX, if Q = —OH in a suitable solvent under an inert atmosphere in the presence of an effective amount of a thallium catalyst, the polyester being Ar—{COO—ρ}$_w$ or Ar—{OOC—ρ}$_w$ wherein ρ is selected from the group consisting of D$_i$ϕ— i is 1 or 2;

ϕ is phenylene

D is selected from the group consisting of:

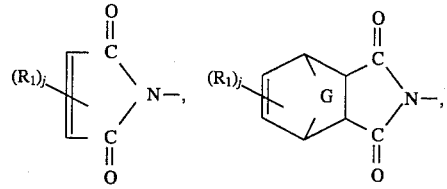

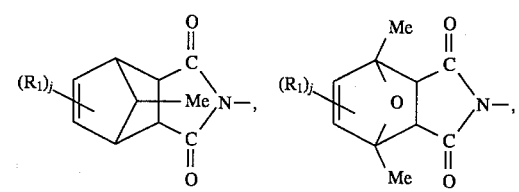

-continued
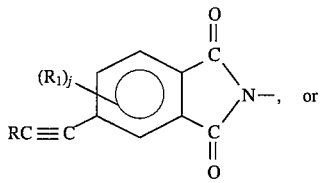, or
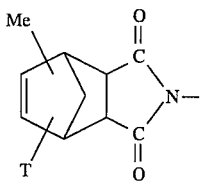
$R_1$ is lower alkyl, aryl, substituted alkyl, substituted aryl, lower alkoxy, aryloxy, halogen, or mixtures thereof;
G is —O—, —S—, —SO$_2$—, —CH$_2$—, —CO—, —CHR—, —SO—, or —C(R)$_2$—;
j is 0, 1, or 2;
T is allyl or methallyl;
Me is methyl; and
R is hydrogen, lower alkyl, or phenyl.
* * * * *